(12) United States Patent
Jo et al.

(10) Patent No.: US 6,884,778 B2
(45) Date of Patent: Apr. 26, 2005

(54) BIOCOMPATIBLE MACROMERS

(75) Inventors: Seongbong Jo, Houston, TX (US); Antonios G. Mikos, Houston, TX (US)

(73) Assignee: William Marsh Rice University, Houston, TX (US)

( * ) Notice: Subject to any disclaimer, the term of this patent is extended or adjusted under 35 U.S.C. 154(b) by 265 days.

(21) Appl. No.: 09/845,570

(22) Filed: Apr. 30, 2001

(65) Prior Publication Data

US 2002/0028189 A1 Mar. 7, 2002

Related U.S. Application Data

(63) Continuation-in-part of application No. 09/549,483, filed on Apr. 14, 2000, now Pat. No. 6,306,821.
(60) Provisional application No. 60/203,689, filed on May 11, 2000, and provisional application No. 60/236,099, filed on Sep. 28, 2000.

(51) Int. Cl.⁷ .......................... A61K 38/16; A61K 9/70
(52) U.S. Cl. .................. 514/12; 424/1; 424/78.08; 424/78.17; 424/484; 424/486; 424/488; 514/2; 528/306
(58) Field of Search ................ 424/484, 486, 424/488, 78.08, 78.17, 1; 514/2, 12, 18; 528/306; 525/54.1, 51.2, 54.24, 54.3, 55, 403, 404; 527/200, 201, 300, 313

(56) References Cited

U.S. PATENT DOCUMENTS

| | | | |
|---|---|---|---|
| 5,162,430 A | 11/1992 | Rhee et al. | 525/54.1 |
| 5,527,864 A | 6/1996 | Suggs et al. | 525/444 |
| 5,573,934 A | 11/1996 | Hubbell et al. | 435/177 |
| 5,644,005 A | 7/1997 | Suggs et al. | 525/444 |
| 5,780,426 A * | 7/1998 | Palladino et al. | 514/9 |
| 5,874,500 A | 2/1999 | Rhee et al. | 525/54.1 |
| 5,945,457 A | 8/1999 | Plate et al. | 514/772.1 |
| 5,986,043 A | 11/1999 | Hubbell et al. | 528/354 |
| 5,998,362 A | 12/1999 | Feng et al. | 514/2 |
| 6,028,164 A | 2/2000 | Loomis | 528/554 |
| 6,248,363 B1 * | 6/2001 | Patel et al. | 424/497 |
| 6,306,821 B1 * | 10/2001 | Mikos et al. | 514/2 |
| 6,596,267 B1 * | 7/2003 | Hubbell et al. | 424/78.26 |

OTHER PUBLICATIONS

Jo et al., "Modification of Oligo(poly(ethylene glycol) fumarate) Macromer with a GRGD Peptide for the Preparation of Functionalized Polymer Networks," Biomacromolecules 2001, 2, 255–261.*
PCT International Search Report for International App. No. PCT/US01/14910: Dated Aug. 2, 2001; (4 p.).

* cited by examiner

*Primary Examiner*—Robert A. Wax
(74) *Attorney, Agent, or Firm*—Conley Rose, P.C.

(57) ABSTRACT

A new oligomer based on alternating fumaric acid and poly(ethylene glycol) (PEG) units is provided. The oligo (PEG fumarate) (OPF) may be functionalized by modification with a biocompatible organic group. Further, the OPF may be cross-linked using radical polymerization in the presence of either a chemical or photo initiator. A cross-linked OPF gel has a swelling behavior that is tunable dependent on the molecular weight of PEG. A cross-linkable PEG macromer, as exemplified by oligo(PEG fumarate), has unsaturated double bonds, for example in the fumaryl groups, along its macromolecular chain that allows for the preparation of hydrogels with tailored structure and properties.

13 Claims, 14 Drawing Sheets

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: YIGSR

<400> SEQUENCE: 1

Tyr Ile Gly Ser Arg
1               5

-continued

```
<210> SEQ ID NO 2
<211> LENGTH: 4
<212> TYPE: PRT
<213> ORGANISM: Artificial Sequence
<220> FEATURE:
<223> OTHER INFORMATION: REDV

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: IKVAV

<400> SEQUENCE: 3

Ile Lys Val Ala Val
1               5

<210> SEQ ID NO 4
<211> LENGTH: 4
<212> TYPE: PRT
<213> ORGANISM: Artificial Sequence
<220> FEATURE:
<223> OTHER INFORMATION: KRSR

<400> SEQUENCE: 4

Lys Arg Ser Arg
1

<210> SEQ ID NO 5
<211> LENGTH: 4
<212> TYPE: PRT
<213> ORGANISM: Artificial Sequence
<220> FEATURE:
<223> OTHER INFORMATION: GRGD

<400> SEQUENCE: 5

Gly Arg Gly Asp
1
```

BIOCOMPATIBLE MACROMERS

CROSS-REFERENCE TO RELATED APPLICATIONS

This application is a continuation-in-part application of U.S. patent application Ser. No. 09/549,483, filed Apr. 14, 2000 now U.S. Pat. No. 6,306,821, and claims the benefit of U.S. Provisional Applications Ser. No. 60/203,689, filed May 11, 2000, entitled "Poly(Ethylene Glycol) Macromer" and Ser. No. 60/236,099, filed Sep. 28, 2000, entitled "Oligo(Poly(Ethylene Glycol) Fumarate", all of which applications are hereby incorporated herein by reference.

STATEMENT REGARDING FEDERALLY SPONSORED RESEARCH OR DEVELOPMENT

This work was supported by funding from the National Institutes of Health Grants R01-AR44381 and R01-DE13031.

FIELD OF THE INVENTION

The present invention relates to a compound for forming a biocompatible polymeric material. More particularly, the present invention relates to a compound that includes an oligo(poly(ethylene glycol) fumarate) (OPF), and a method for making same. Further, the present invention relates to compounds including OPF that may be functionalized by modification with a therapeutic agent, such as a biocompatible organic group, and/or may be cross-linked to form a polymeric network.

BACKGROUND OF THE INVENTION

Synthetic, degradable polymeric networks have found utility as biomaterials in a variety of medical applications. For example, degradable polymeric networks can be used as carriers for delivery of therapeutic agents, such as gene therapy agents, drugs, and biocompatible organic compounds that modify cellular function. In particular, degradable polymeric networks can serve as conduits for guided tissue regeneration, such as in wound healing. Further, degradable polymeric networks can serve as supportive scaffolding for cells, such as in bone regeneration and repair. Still further, degradable polymeric networks can serve as stimulants of desired cellular responses and as specific substrates for targeted cell adhesion, among other cellular applications.

Degradable polymeric networks that are useful in biomedical applications are typically based on polymers that are desirably nontoxic and biocompatible. Poly(ethylene glycol) (PEG), a hydrophilic polyether, is one such polymer. Water-soluble polymers such as PEG, have been investigated extensively in recent years for use as nontoxic, biocompatible, protein repulsive, noninflammatory, and nonimmunogenic modifiers for drugs, proteins, enzymes, and surfaces of implanted materials. The solubility of PEG in water as well as a number of common organic solvents facilitates its modification by a variety of chemical reactions and makes it useful for binding water-insoluble or poorly water-soluble molecules and rendering them water-soluble.

Formation of a degradable polymeric network from PEG typically involves chemical modification of the PEG in order to form a cross-linkable macromer. The chemical modification may take a variety of forms, typically involving bonding the PEG to a cross-linkable moiety. When the macromers are cross-linked together, a polymeric network is formed that includes the cross-linkable moieties, as well as PEG polymer units. Polymeric networks based on PEG may differ in their properties, depending for example on the nature of the cross-linking and the presence of any co-polymers.

Poly(ethylene glycol) (PEG) based macromers have been extensively investigated for use in hydrogel preparation. Hydrogels swell in water and have been investigated particularly as carriers of therapeutic agents. Hydrogels have the advantages that they diminish non-specific adherence of carried agents to cells. Thus, they can be made cell-adhesion specific through the introduction of specific attached molecules, or ligands.

Typically, PEG macromers have been based on (meth)acrylation of PEG based polymers, where the (meth)acrylate group functions as the cross-linkable moiety. PEG di-(meth)acrylate has been cross-linked by photoirradiation, among other methods. The photo-cross-linking of PEG acrylates has been extensively explored as a method of coating PEG onto surfaces of polymeric materials and biological tissues. A disadvantage of PEG acrylates, such as PEG methacrylates, for use in forming a degradable polymeric network is that hydrolysis of a PEG acrylate macromer liberates ethylene glycol and an acrylic acid, such as methacrylic acid. Methacrylic acid is toxic and thus not biocompatible. Further, PEG mono- and di-(meth)acrylates have a tendency to form clumped polymeric networks, due to the cross-linkable moiety being present at one or both ends of the macromer.

An alternative type of PEG macromer based on the photodimerization of cinnamylidene groups has also been synthesized. This light-sensitive PEG macromer has been cross-linked by long wavelength (>300 nm) UV irradiation, however, the photo-cross-linked PEG hydrogels can undergo photoscission with UV irradiation at 254 nm. Various proteins such as myoglobin, hemoglobin, lactate dehydrogenase, and organophosphorous hydrolase have been immobilized into the photosensitive hydrogels and their stability has been demonstrated.

Nothwithstanding the above teachings, it is desirable to provide PEG-based polymeric networks that are biodegradable, have desired mechanical properties in both wet and dry states, and that degrade into non-toxic degradation products.

SUMMARY OF THE INVENTION

The present invention includes a macromer that is formed of at least two repeating units that each contain a biocompatible cross-linkable moiety bound to a biocompatible polymer. A preferred biocompatible polymer is PEG. Further, a preferred biocompatible cross-linkable moiety is a fumaryl group.

The present invention includes a macromer based on PEG and fumaric acid. This new PEG macromer has different properties from previous PEG macromers. The macromer may also be advantageous for biodegradation because of its multiple ester bonds in comparison with PEG (meth)acrylates. The macromer is further expected to be biocompatible because it consists of biocompatible components. Since the PEG macromer based on fumaric acid is composed of monomeric PEG fumarate of finite length, the physical properties of the macromer can be easily tailored by changing PEG molecular weight.

The present invention includes a method of making a PEG macromer that involves a one-pot reaction between PEG and fumaryl chloride. This reaction may be useful for other applications. Further, the reaction can be influenced by factors such as PEG molecular weight and reactant molar ratio. The interpretation and modulation of those factors involved in the condensation reaction will provide useful information that is applicable to the preparation of various macromers with desirable properties as well as the resulting hydrogels.

The present invention includes any of the above macromers modified by the addition of a therapeutic agent. The therapeutic agent may be any conventional therapeutic agent, such as drugs, gene therapy agents, molecules that modulate cell function, and the like. Molecules that modulate cellular function may be biocompatible organic groups, such as peptides, proteins, protein fragments, proteoglycans, glycoproteins, and carbohydrates, and the like.

The present invention includes a method for the preparation of a polymeric network functionalized with various bioactive molecules. The base macromer for the method preferably is composed of biocompatible PEG and fumaric acid. A preferred polymeric network is advantageous for biodegradation because of the inclusion of multiple ester bonds. Further, the unsaturated fumarate bonds of a preferred macromer have the advantage of being useful for preparation of polymeric composites with controlled mechanical properties by radical polymerization.

Thus, the present invention includes a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying Figures, wherein.

DETAILED DESCRIPTION OF A PREFERRED EMBODIMENT

According to a preferred embodiment of the present invention, a biodegradable macromer includes a plurality of repeating units. Each repeating unit preferably includes a biocompatible polymer of finite, predetermined length and a biocompatible cross-linkable moiety. Thus, when the preferred macromers are cross-linked, a controllable macromolecular structure is preferably provided. For example, the preferred macromers can be used to form a network structure with a mesh size that can be tuned by varying the molecular weight of the polymers that are combined with cross-linkable moieties to form the macromer. Further, when the preferred macromers are cross-linked, a polymeric network is preferably provided that has controllable properties. For example, the wet to dry swelling ratio of a hydrogel formed by cross-linking the preferred macromers is preferably tunable by varying the molecular weight of the polymer used to form the macromer.

The polymer preferably includes poly(ethylene glycol) (PEG). Further, the cross-linkable moiety preferably includes an unsaturated carbon carbon bond. More preferably the cross-linkable moiety includes a fumaryl group that includes the unsaturated bond.

Figure 1:
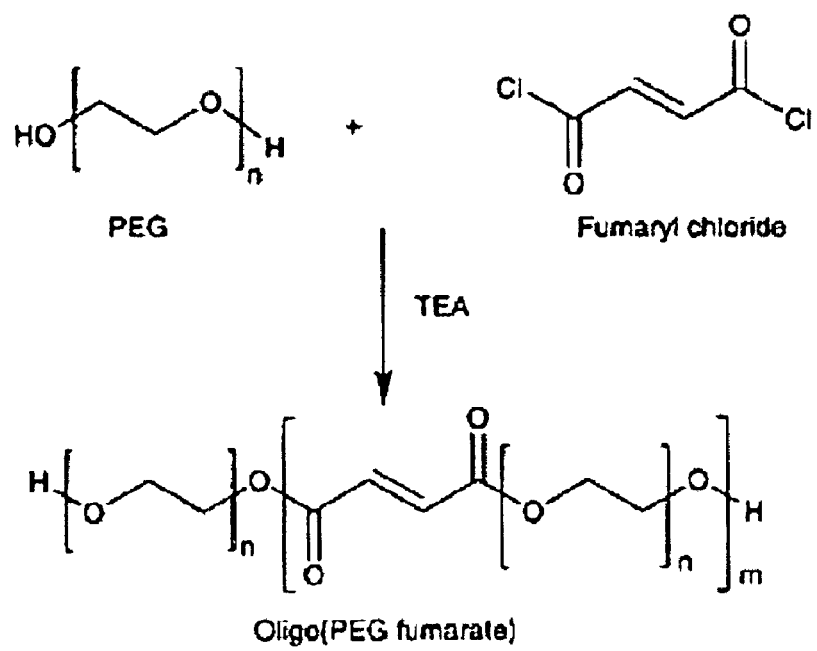
FIG. 1 is a schematic chemical diagram illustrating the synthesis of oligo(poly(propylene glycol)fumarate) (OPF)

In particular, referring to now to FIG. 1, according to a preferred embodiment of the present invention, a new biodegradable PEG macromer is prepared by a one-pot reaction between PEG and a fumaryl compound. The fumaryl compound preferably has a substituent, such as a Lewis base that has an affinity for hydrogen. In the reaction, a hydrogen is removed from the PEG and the substituent is removed from the fumaryl compound. The reaction is preferably carried out in the presence of an organic base, as a solvent. The solvent preferably acts as a proton scavenger. A suitable organic base is, for example, triethylamine. The reaction between PEG and fumaryl chloride preferably results in the formation of PEG fumarate oligomers. These are oligo(PEG fumarate) (OPF) and are the preferred macromers of the present invention.

According to a preferred embodiment of the present invention, an OPF macromer is terminated by PEG. Macromers with these end PEG chains are preferred for the immobilization of proteins and peptides due to their terminal hydroxyl groups. These macromers may also be utilized to produce hydrogels with specific functions, such as molecular recognition and drug delivery. However, it will be understood that, in other embodiments of the present invention, the macromer may be terminated by fumarate.

It will be understood that the other polymeric units may be used as alternatives to PEG. In particular, PEG is exemplary of polyethers, in particular hydrophilic polyethers. Further, any suitable end-hydroxylated polymer may be used. For example, the previously described reaction can be used to prepare biodegradable macromers based on fumaric acid by reacting biodegradable polymers with end functional groups such as end-hydroxylated polycaprolactone and end-hydroxylated poly(α-hydroxy acid)s in the presence of fumaryl chloride.

According to some embodiments of the present invention, the oligo(poly(ethylene glycol) fumarate) (OPF) macromer is cross-linked to form a polymeric network. The cross-linked OPF may be especially valuable for the surface coating of polymeric materials by photoirradiation. Cross-linking may be direct, from the fumaryl of an OPF to the fumaryl of another (or the same) OPF. Alternatively, cross-linking may be indirect, involving a linker molecule cross-linked to the OPF. Exemplary linker molecules are PEG-diacrylate and PPF-diacrylate, where PPF stands for poly(propylene fumarate). It is preferred that the linker molecule is biocompatible. Further, the linker molecule preferably is degradable to non-toxic components.

In some embodiments of the present invention, an OPF is copolymerized with other monomers. The co-polymerization of OPF with other monomers is preferably useful for the preparation of polymeric gels with different physical properties from a gel prepared by polymerization of OPF without co-polymerization. The properties preferably depend on the other monomer. Further, the co-polymer is preferably chosen from among any known biocompatible polymeric monomer according to a desirable physical property of the gel formed by co-polymerizing the monomer with OPF to form a macromer according to an embodiment of the present invention.

In some embodiments of the present invention, a cross-linked OPF has tunable swelling properties. An OPF according to a preferred embodiment of the present invention, has different swelling properties from hydrogels of PEG acrylates or P(PF-co-EG), since fumarate bonds in the OPF are separated by finite PEG blocks. A preferred OPF, therefore, has the advantage of being more suitable for preparing hydrogels with a defined structure. In particular, an advantage of the OPF is the ability to form polymeric networks having a controlled macromolecular structure. An example of a desirable structure that may be obtained is a mesh structure with a controllable mesh size.

Furthermore, the presence of multiple ester bonds as well as hydrophilic PEG backbones in a preferred OPF can facilitate the degradation of OPF in an aqueous environment.

Still further, a preferred OPF has the advantage of being suitable for use as a cross-linking agent for polymeric resins. For example, an OPF according to a preferred embodiment of the present invention improves the dispersion of polymeric resins because it is soluble in aqueous and organic solvents.

Figure 3:
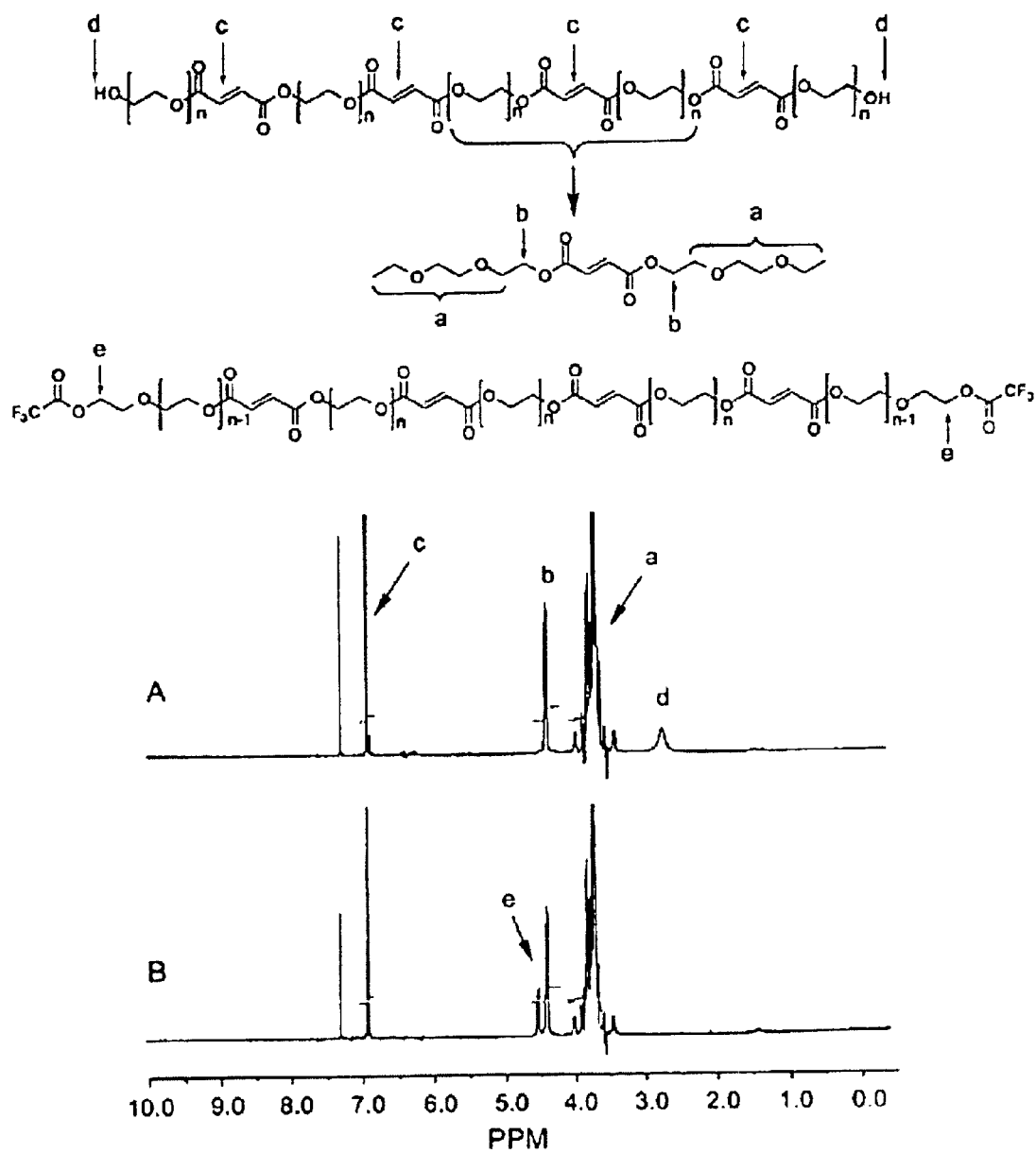
FIG. 3 is a plot showing $^1$H NMR spectra of an OPF 1.0K in the absence (A) and presence (B) of trifluoroacetic anhydride, where the OPF 1.0K was prepared by the reaction between PEG 1.0K and fumaryl chloride at a 1:0.90 molar ratio, and the NMR measurements were carried out in CDCl$_3$ at room temperature.

Referring now to FIG. 3, a preferred method of modification of OPF with a therapeutic agent, such as a bioactive molecule, is by reacting the end hydroxl groups of PEG with 4-nitrochloroformate (NPC) to form an activated NPC-OPF.

Alternatively, OPF may also be modified with a therapeutic agent through an N-hydroxysuccinimidyl (NHS) ester. Although the modification of the NHS activated OPF (NHS-OPF) may be faster than that of the NPC-OPF, the terminal group of OPF preferably includes carboxylic acid groups instead of hydroxyl groups. An OPF with end carboxylic acid groups can be obtained by the reaction with a molar excess of fumaryl chloride over PEG that results in OPF with end fumaric acids rather than PEG, or by succinylation of end hydroxyl groups of OPF with succinic anhydride. However, the succinylation will be an additional step to prepare the activated OPF and the OPF with fumaric acids, different from the OPF with PEG, will eventually result in the incorporation of peptides with limited mobility in polymeric scaffolds by the absence of a flexible PEG spacer with the cross-linking of end fumaric acids.

The therapeutic agent may be any conventional therapeutic agent for example molecules that modulate cellular function, such as biocompatible organic groups, for example peptides, proteins, protein fragments, proteoglycans, glycoproteins, and carbohydrates.

Suitable peptides include RGD, YIGSR, REDV, IKVAV, and KRSR peptides. In particular, RGD peptides have been known to modulate cell behavior on a variety of surfaces and are therefore considered useful for cell-modulating polymeric networks. NPC-OPF has cross-linkable fumarate bonds as well as 4-nitrophenylcarbonate groups for peptide coupling, making it ideal for the preparation of polymeric networks functionalized with cell specific peptides.

Further, the presence of cross-linkable double bonds in an OPF modified with a peptide may be advantageous for many biomedical applications because it can be formed into cross-linked polymeric networks that are functionalized with bioactive peptides. Although the example described below in Section II utilized GRGD to functionalize OPF, many other molecules such as specific growth factors or fragments thereof may be incorporated into the polymer networks.

Suitable proteins include members of the transforming growth factor beta superfamily, bone morphogeneic proteins, basic fibroblast growth factor, platelet derived growth factor, insulin like growth factor, and extracellular matrix molecules including osteopontin, osteonectin, osteocalcin, and bone sialoprotein. Suitable protein fragments include fragments of the members of the same compounds, comprising 3–30 amino acids.

Suitable carbohydrates include starch, cellulose, and chitin.

The cross-linked PPF carrying cell adhesion peptides may find applications in biomaterials. Cross-linked PPF has favorable mechanical properties for orthopaedic applications, as disclosed for example in commonly assigned co-pending U.S. patent application Ser. No. 09/549,483, filed Apr. 14, 2000, entitled "Functionalized Poly(Propylene Fumarate and Poly(Propylene Fumare-co-Ethylene Glycol", which is incorporated herein by reference, commonly assigned co-pending U.S. patent application Ser. No. 09/549,485, filed Apr. 14, 2000, entitled Biodegradable Poly(Propylene Fumarate) Networks Cross Linked WithPoly(Propylene Fumarate)Diacrylate Macromers, hereby incorporated herein by reference, and commonly assigned co-pending U.S. patent application Ser. No. 09/550,372, filed Apr. 14, 2000, entitled Poly(Propylene Fumarate) Cross-Linked with Poly(Ethylene Glycol), hereby incorporated herein by reference. The functionalized OPF will be especially effective for the preparation of polymeric networks with modulated cellular functions, since the PEG chain between peptide and fumarate will serve as a flexible spacer that can stretch out to a biological solution and facilitate the interaction between cells and peptides.

Without further elaboration, it is believed that one skilled in the art can, using the description herein, utilize the present invention to its fullest extent. The following specific embodiments are to be construed as illustrative and not as constraining the scope of the present invention in any way whatsoever.

EXAMPLES

I. Oligo(Poly(Ethylene Glycol)Fumarate)Macromers

Materials

PEG (MW=1000, 3350, and 4600) (PEG 1.0K, 3.4K, and 4.6K, respectively), trifluoroacetic anhydride (TFAA), N-vinyl-2-pyrrolidinone (NVP), calcium hydride, ammonium persulfate, and triethylamine were purchased from Aldrich (Milwaukee, Wis.). Fumaryl chloride was obtained from Acros (Pittsburgh, Pa.) and distilled before use. Anhydrous methylene chloride was obtained by distillation after the reflux for 2 h in the presence of calcium hydride. Ascorbic acid was obtained from Sigma (Saint Louis, Mo.) and bis-(2,4,6-trimethylbenzyl) phenylphosphine oxide was given by Ciba Specialty Chemicals (Terrytown, N.Y.). Other solvents were of reagent grade and were used without purification.

General Procedures

Synthesis of Oligo(PEG Fumarate) (OPF)

OPF was prepared by the reaction schematically represented in FIG. 1. Thirty grams (0.003 mole) of PEG 1.0K (50 g for PEG 3.4K and 4.6K) was dried by azeotropic distillation as follows. After dissolving PEG in 250 ml of toluene, 150 ml of toluene was distilled off and the remaining toluene was further removed under reduced pressure. The dried PEG 1.0K was dissolved in 250 ml of anhydrous methylene chloride. Fumaryl chloride (0.3 mole) and triethylamine (0.3 mole) were simultaneously added to the PEG solution in an ice bath over 5 h while the reaction mixture was vigorously stirred. For the oligomerization of PEG 3.4K and 4.6K, 500 ml of anhydrous methylene chloride was used. To investigate the effect of the reactant ratio on the OPF molecular weight, three different molar ratios of PEG 1.0K to fumaryl chloride were used (1:0.8, 1:0.9, and 1:0.98). OPF from PEG of different molecular weights (OPF 1.0K, 3.4K, and 4.6K from PEG 1.0K, 3.4K, and 4.6K) was prepared by the same reaction for PEG 1.0K at 1:0.9 molar ratio of PEG to fumaryl chloride. After dropwise addition of fumaryl chloride and triethylamine into the PEG solution, the reaction was run overnight at room temperature. Upon completion of the reaction, the solvent was removed by rotovaporation and the residue was dissolved in 500 ml (1000 ml for OPF from PEG 3.4K and 4.6K) of warm ethyl acetate. Then, triethylamine hydrochloride salt was removed by filtration. The OPF was recrystallized twice from ethyl acetate and dried at reduced pressure. The OPF was kept in a refrigerator to avoid crosslinking at room temperature.

Characterization of OPF

The PEG macromers were characterized by a 250 MHz $^1$H NMR (Bruker AC 250) in CDCl$_3$. The end group of OPF was analyzed by NMR measurements after dissolving the OPF with 5.0% v/v trifluoroacetic anhydride in CDCl$_3$. The number average molecular weight of OPF was calculated from the NMR spectra.

The OPF was analyzed by differential scanning calorimetry (DSC). DSC was performed on a TA Instruments Model 2920 (Newcastle, Del.) with a mechanical cooling accessory. The samples were analyzed at a heating rate of 10° C. per min from 0 to 70° C. Melting points and the heat of fusion, $\Delta H_m$ (cal/g), were obtained from the thermograms. The percent crystallinity of OPF, X, was determined from the following equation:

$$X = \frac{\Delta H_m}{\Delta H_m^*} \times 100 \tag{1}$$

Here, $\Delta H_m^*$ is the theoretical heat of fusion of 100% crystalline PEG (49 cal/g).

The molecular weight of OPF was also calculated by gel permeation chromatography (GPC). A Phenogel guard column (50×7.8 mm, 5 μm, mixed bed, Phenomenex, Torrence, Calif.) and a Phenogel column (300×7.8 mm, 5 μm, mixed bed, Phenomenex) were used to elute the samples at 1 ml per min chloroform flow rate. After obtaining the calibration curve with PEG standards (Polyscience, Warrington, Pa.), number-average ($M_n$) and weight-average ($M_w$) molecular weights were calculated by running OPF samples. The degree of oligomerization, $\bar{X}n$, and the conversion of OPF, p, were determined by the following equations:

$$\bar{X}_n = \frac{M_{n,OPF}}{M_{n,PFU}} \tag{2}$$

$$\bar{X}_n = \frac{1+r}{1+r-2rp} \tag{3}$$

Here, $M_{n,OPF}$, $M_{n,PFU}$, and r represent the $M_n$ of OPF determined by GPC, the molecular weight of monomeric PEG fumarate, and [fumaryl chloride]/[PEG], respectively.

The OPF was characterized by FT-IR spectroscopy. Samples were prepared as KBr pellets and the spectra were obtained on a Nicolet 500 spectrometer (Madison, Wis.).

Cross-Linking of OPF and Characterization of the Photo-Cross-Linked OPF Hydrogels The OPF was cross-linked by radical polymerization. The cross-linking of the OPF was qualitatively analyzed by NMR measurements. To observe the cross-linking of OPF by photoirradiation, 0.2 g of OPF 3.4K and 0.002 g of bis-(2,4,6-trimethylbenzyl) phenylphosphine oxide were dissolved in 1.0 ml of CD$_3$OD:DMSO-d$_6$ (1:1). The NMR spectrum of the OPF solution was recorded before and after 30 min photoirradiation in an Ultralum (Paramount, Calif.) ultraviolet light box. The cross-linking of OPF by the chemical initiators was investigated after dissolving 0.2 g of the OPF and 5.0 μg of ammonium persulfate and ascorbic acid in 1 ml of D$_2$O. The NMR spectrum of the OPF solution was recorded at 10 min, 1.5 h, 3.0 h, and 24 h after the addition of initiators.

The swelling of the cross-linked OPF was investigated by a gravimetric method. Samples for the swelling study were prepared by photoirradiation which was faster than chemical cross-linking. The solution for cross-linking was prepared by dissolving 1 g of OPF in 5 ml of 60% v/v dimethylformamide (DMF) in water. To investigate the effect of the amount of photoinitiator, 0.1, 0.15, and 0.2 ml of 10 w/v % bis-(2,4,6-trimethylbenzoyl) phenylphophine oxide in DMF were mixed with the OPF solution. The OPF solution was transferred to a polystyrene cell culture dish (60×15 mm, Fisher Scientific, Pittsburgh, Pa.) lined with Teflon film. The OPF solution was cross-linked by 1 h irradiation with UV light. The cross-linked OPF gels were cut into 12 mm diameter discs. The disks were dried at 0.25 torr overnight and then weighed, $W_i$. The dry films were swollen in 20 ml of deionized distilled water (DDW) until an equilibrium was reached then weighed again, $W_s$. The swollen gels were dried overnight at reduced pressure and weighed, $W_d$. The swelling ratio and the fraction of unreacted macromer, sol fraction, were determined by the following equations.

$$\text{Swelling Ratio} = \frac{W_s - W_d}{W_d} \quad (4)$$

$$\text{Sol Fraction} = \frac{W_i - W_d}{W_i} \quad (5)$$

Here, swelling ratio represents the amount (g) of water that can be drawn by 1 g of dry OPF gel rather than simple weight ratio between swollen and dry OPF gels.

Results

As described in more detail below, end group analysis by nuclear magnetic resonance (NMR) spectroscopy showed that the oligo (PEG fumarate) (OPF) had end PEG chains and multiple fumarate groups along its macromolecular chain. According to thermal characterization by differential scanning calorimetry (DSC), the crystallinity of OPF was found to be lower than PEG. The molecular weight and the degree of oligomerization of OPF determined by gel permeation chromatography (GPC) revealed that the conversion of OPF was substantially affected by the steric factors associated with large PEG chains. As the OPF was crosslinked, the unsaturated fumarate bonds disappeared and the PEG proton peak broadened in the NMR spectra.

Characterization of OPF

The end group of the OPF was analyzed by using trifluoroacetic anhydride, a compound that immediately reacts with free hydroxyl groups to form trifluoroacetate. The formation of trifluoroacetate shifted the attached methylene proton downfield, thus separating it from the other methylene proton peaks of PEG (FIG. 3). Since trifluoroacetic anhydride can not react with fumaric acid, this change in the NMR spectrum indicated the presence of end hydroxyl groups and therefore the termination of OPF by PEG.

Figure 4:
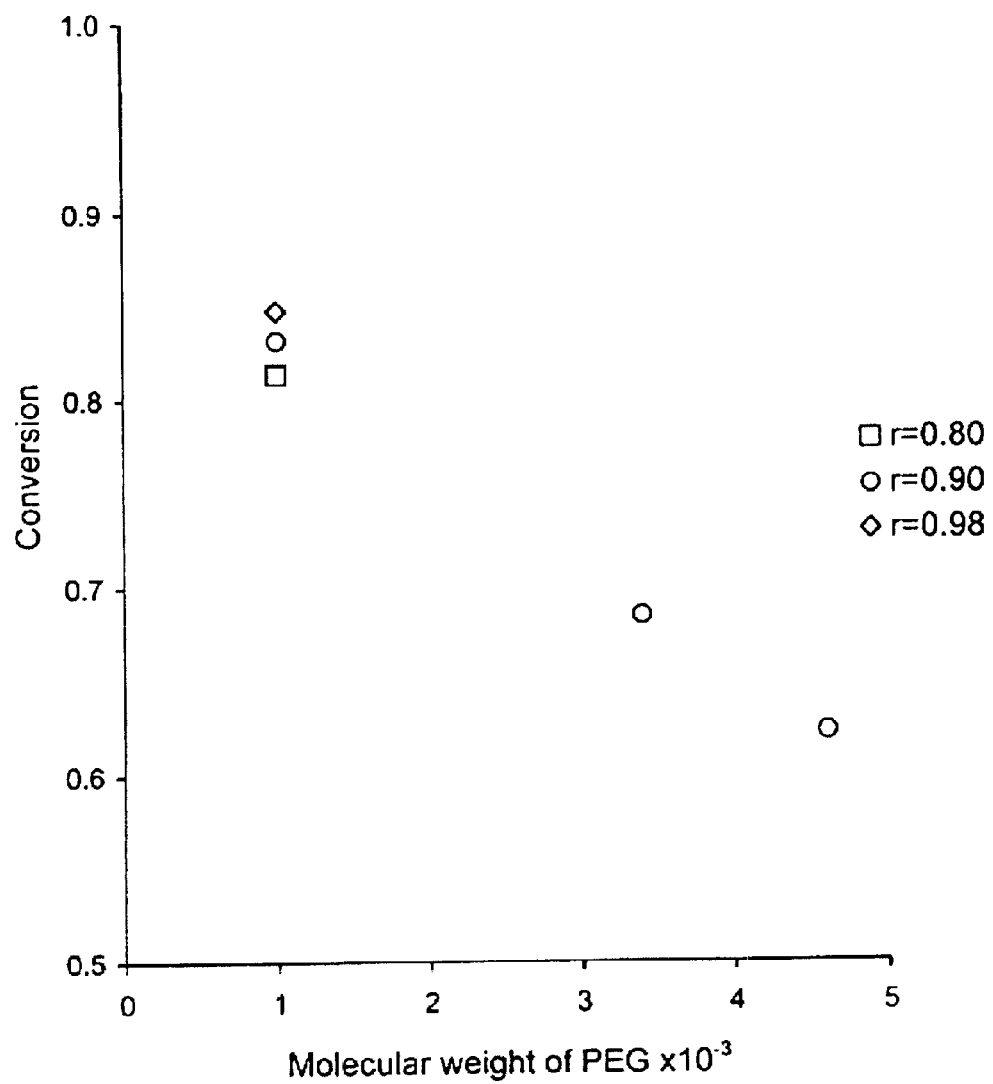
FIG. 4 is a plot showing measured conversion of OPF prepared from PEG 1.0K (for r=0.80, 0.90, 0.98), 3.4K, and 4.6K.
Figure 5:
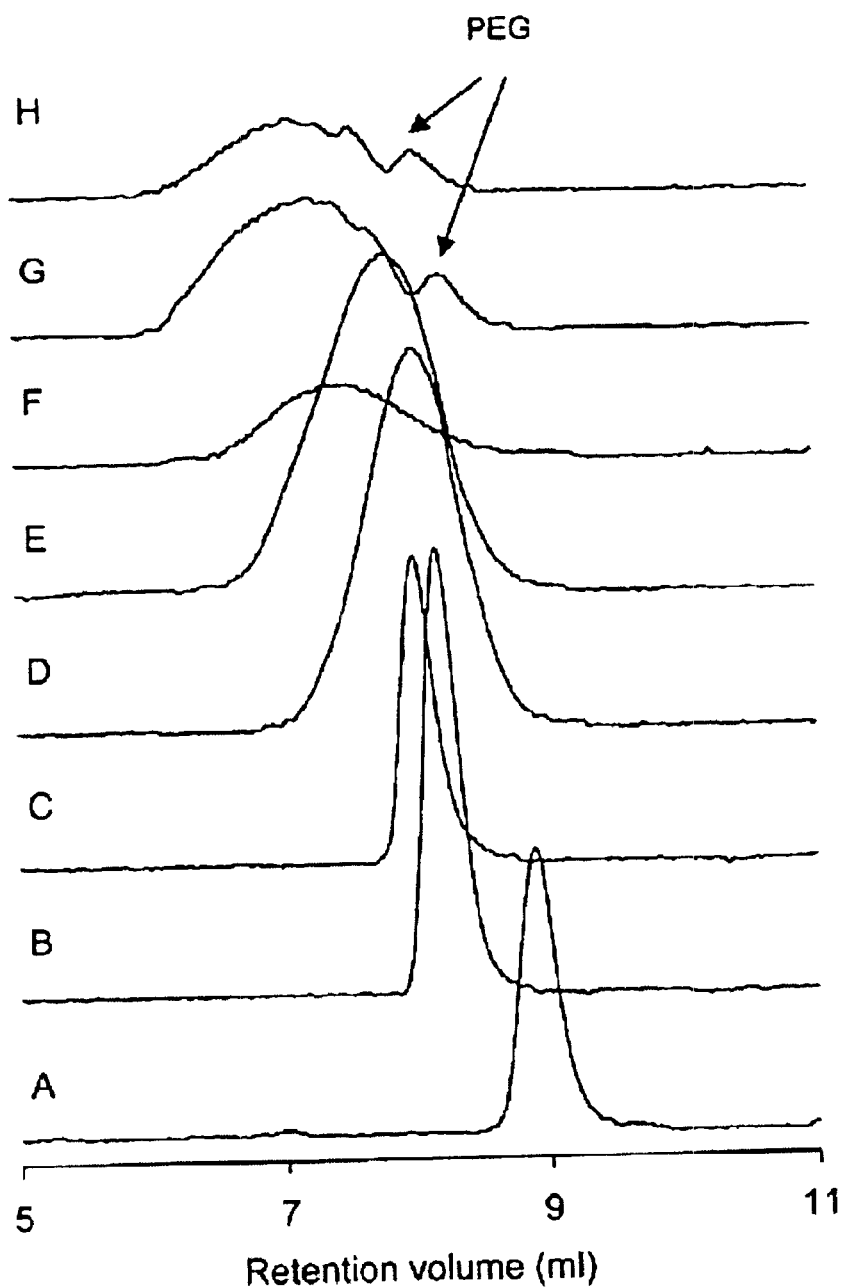
FIG. 5 is a plot showing GPC chromatograms of PEG and OPF, where PEG 1.0K (A), 3.4K (B), and 4.6K (C) were used for the preparation of OPF 1.0K at 1:0.80 (D), 1:0.90 (E), and 1:0.98 (F) molar ratio between PEG and fumaryl chloride, OPF 3.4K (G), and OPF 4.6K (H) at 1:0.90 molar ratio between PEG and fumaryl chloride.
Figure 6:
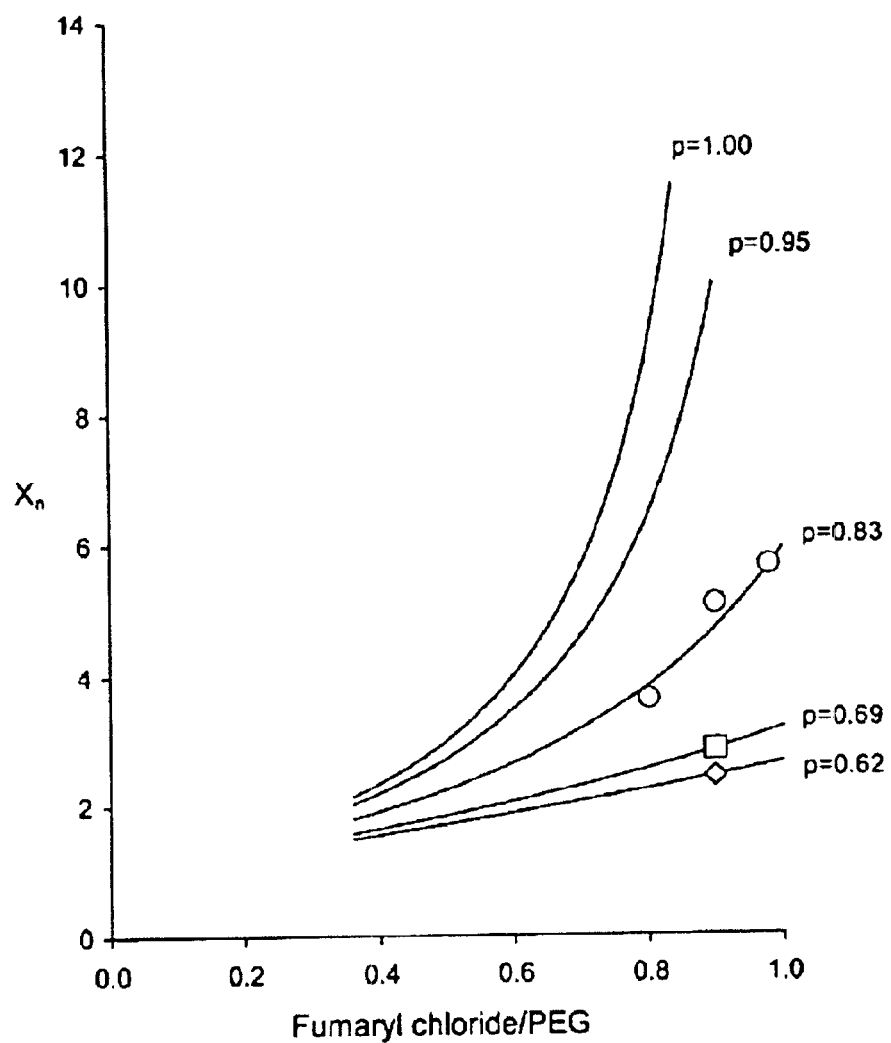
FIG. 6 is a plot showing dependence of the degree of oligomerization, $\overline{X}n$, on the conversion, p, and monomer molar ratio, r, where the degree of oligomerization at various conversions was calculated by using equation (3), experimental data were fitted to the curves, and for OPF 1.0K, OPF 3.4K, and OPF 4.6K, the determined p values 0.83, 0.69, and 0.62, respectively, were used.

The number-average molecular weight ($M_n$) of OPF was determined by NMR measurements with the assumption that the OPF had PEG end groups. The determined molecular weights of OPF are presented in Table 1. The OPF molecular weight was close to that determined by GPC calibrated with PEG standards.

chloride. As the PEG molecular weight increased from 1000 to 4600, the $\overline{X}n$ determined by equation (2) decreased from 5.1 to 2.5. As the ratio of fumaryl chloride to PEG, r, decreased from 0.98 to 0.80, $\overline{X}n$ also decreased from 5.67 to 3.6 and the $M_n$ of OPF decreased from 7790 to 4990. The conversion of PEG and fumaryl chloride into OPF (p), as determined by equation (3) decreased as the PEG molecular weight increased. Specifically, as the PEG molecular weight increased from 1000 to 4600, p fell from 0.83 to 0.62 (r=0.9) (FIG. 4). However, a change in r did not cause a significant change in p. The calculated p values for OPF 1.0K at r=0.98, 0.90, and 0.80 were 0.83, 0.85, and 0.81 respectively. These effects of PEG molecular weight on oligomerization extent can be explained in terms of steric hindrance. As PEG molecular weight increases, the reactivity of end hydroxyl groups decreases since the larger PEG random coil exerts more steric hindrance. For example, the GPC chromatograms in FIG. 5 indicate that the OPF 1.0K does not include any noticeable free PEG while OPF 3.4K and 4.6K do contain a small amount of free PEG. The results also show that the hydroxyl groups of low molecular weight PEG are more accessible to fumaryl chloride during the oligomerization. FIG. 6 shows that the OPF molecular weight can be modulated by a change in r. According to the calculated $\overline{X}n$ at various p values, the effect of r on $\overline{X}n$ substantially increases as p is closer to 1.00. In reality, the polycondensation between fumaryl chloride and PEG can not produce oligomers of high molecular weight mainly because of the steric factor of PEG. According to FIG. 5, the highest achievable $\overline{X}n$ in our experimental system was 6.0, 3.2, and 2.7 for PEG 1.0K, 3.4K, and 4.6K, respectively. However, the conversion of OPF may be improved by increasing the reaction time.

Thermal characterization of OPF by DSC showed that the OPF has a lower heat of fusion than PEG. A change in r also affected the heat of fusion of the OPF and thus the crystallinity. As r for OPF 1.0K increases from 0.80 to 0.98, the heat of fusion decreases from 27.0 to 21.2 cal/g. These values are noticeably lower than 28.9 J/g, the heat of fusion of PEG 1.0K determined by DSC. Additionally, the melting temperature of OPF was lower than that of PEG. OPF 3.4K and 4.6K especially showed significant lower melting temperatures than PEG 3.4K and 4.6K while the OPF 1.0K had similar melting temperature to the PEG 1.0K. The melting temperatures of PEG 3.4K and 4.6K were 60.59 and 61.06°

TABLE 1

Characterization Data of Various OPF Prepared From PEG of Different Molecular Weights and Fumaryl Chloride[a]

| Sample | r | $T_m$(° C.) | $\Delta H_m$(cal/g) | % crystallinity | GPC $M_n$ | GPC $M_w$ | GPC $X_n$ | NMR $M_n$ |
|---|---|---|---|---|---|---|---|---|
| PEG 1.0K | | 40.512 ± 1.65 | 28.9 ± 2.8 | 59.0 | 1260 | 1330 | | |
| PEG 3.4K | | 60.59 ± 1.00 | 40.1 ± 0.2 | 81.8 | 3960 | 4180 | | |
| PEG 4.6K | | 61.06 ± 0.78 | 44.2 ± 4.4 | 90.2 | 5080 | 5440 | | |
| OPF 1.0K | 0.98 | 39.42 ± 1.18 | 21.2 ± 2.4 | 43.3 | 7790 | 16070 | 5.67 | 6720 |
| OPF 1.0K | 0.90 | 39.83 ± 0.27 | 25.9 ± 0.5 | 52.9 | 7000 | 11210 | 5.09 | 6840 |
| OPF 1.0K | 0.80 | 40.29 ± 1.01 | 27.0 ± 1.4 | 55.1 | 4990 | 6960 | 3.63 | 4630 |
| OPF 3.4K | 0.90 | 55.47 ± 0.52 | 35.1 ± 2.4 | 71.6 | 11610 | 22060 | 2.85 | 1240 |

[a]r is the molar ratio between fumaryl chloride and PEG. The melting temperature ($T_m$) and the heat of fusion ($\Delta H_m$) were measured by DSC. Number-average ($M_n$) and weight-average ($M_w$) molecular weights were calculated by GPC and end group analysis using NMR. The degree of oligomerization, $X_n$, was determined by eq 3. For DSC measurements, n = 3.

The properties of OPF were dependent on the PEG molecular weight and the ratio between PEG and fumaryl C., while those of OPF 3.4K and 4.6K (r=0.9) were 55.47 and 56.69° C., respectively. The changes in the heat of fusion and melting temperature could be a result of conformational changes in the polymer backbones caused by oligomerization. The incorporation of rigid fumarate bonds could prevent close packing of the flexible PEG chains and thus cause a decrease in crystallinity as seen in Table 1. This decrease in crystallinity may result in the observed changes in melting temperature and heat of fusion in comparison with PEG.

Figure 7:
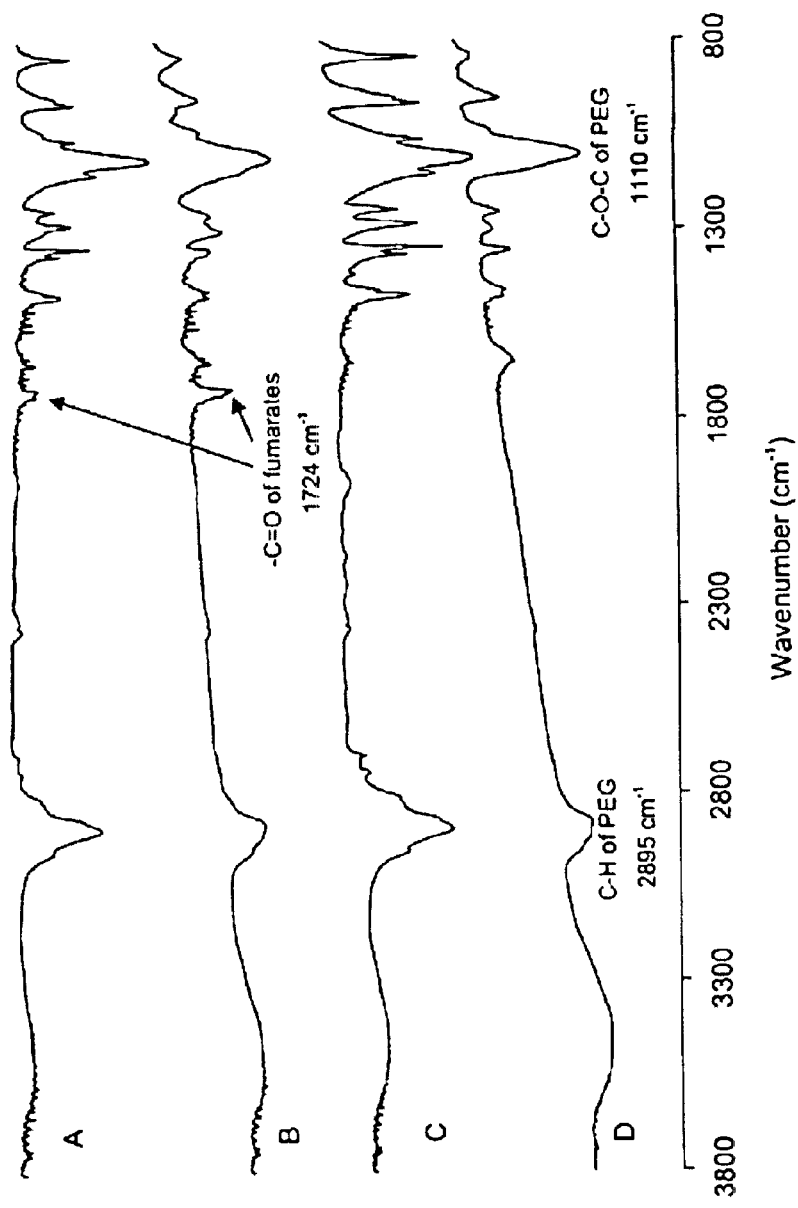
FIG. 7 is a plot showing FT-IR spectra of OPF 3.4K (A) and OPF 1.0K (B) prepared from PEG 3.4K (C) and 1.0K (D).

The FT-IR spectra of OPF in FIG. 7 also indicated successful incorporation of fumarate bonds into the macromer. In comparison with the IR spectra of PEG 1.0K and 3.4K, the IR spectra of corresponding OPF 1.0K and 3.4K showed a characteristic ester carbonyl stretch band at 1725 cm$^{-1}$ in addition to an asymmetrical C—O—C stretching band at 1110 cm$^{-1}$ and C—H stretch bands at 2890 cm$^{-1}$.

Characterization of the Cross-Linking of OPF by NMR

Figure 8:
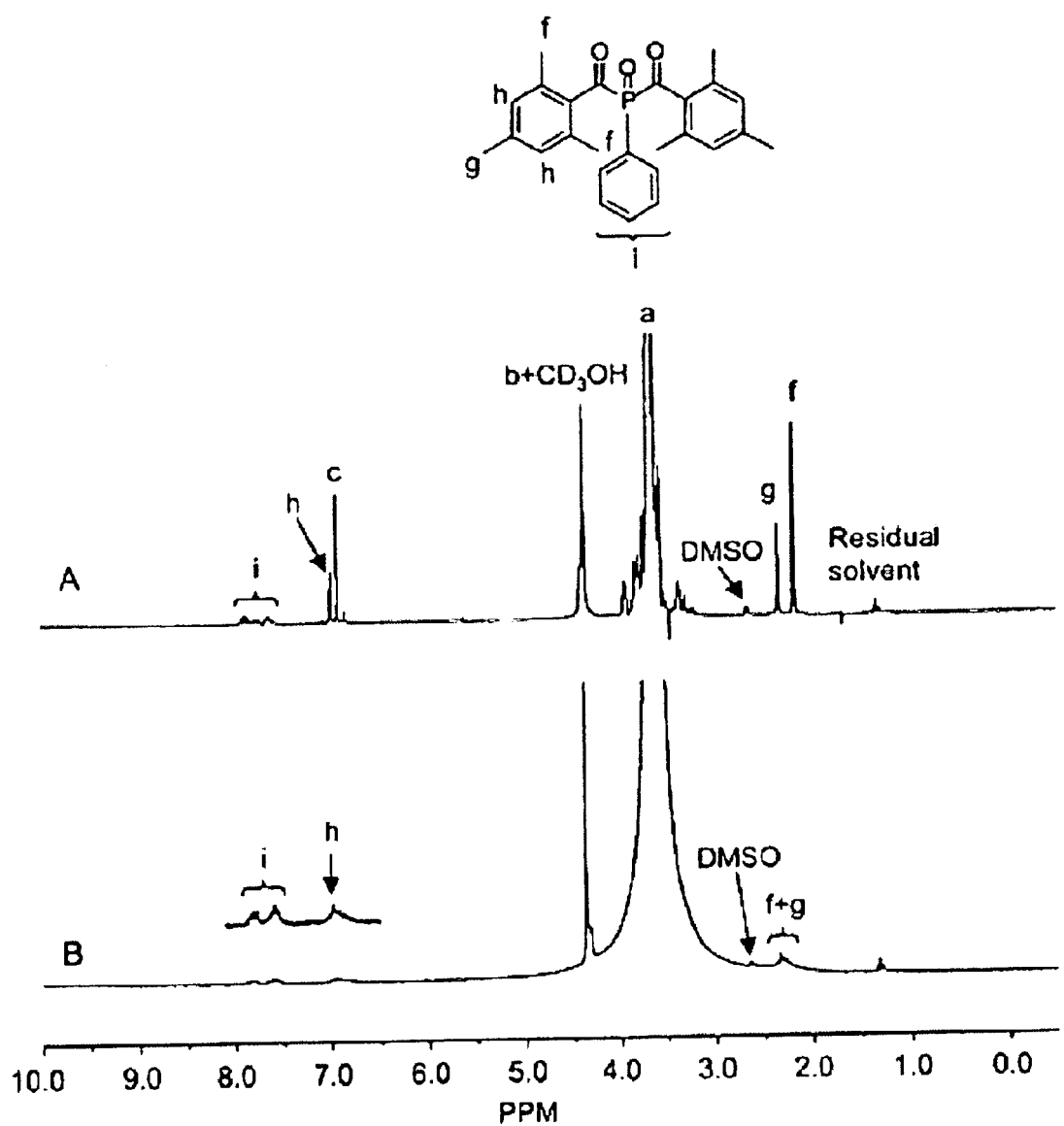
FIG. 8 is a plot showing $^1$H NMR spectra of OPF 3.4K before (A) and after (B) UV irradiation for 30 min in the presence of 1.0% w/w of bis-(2,4,6-trimethylbenzyl) phenylphosphine oxide, where the NMR was measured in CD$_3$OD:DMSO-d$_6$ (1:1) and the peak assignment of OPF was based on the chemical structures and notions in FIG. 3.

The OPF was cross-linked by radical polymerization. The cross-linking of OPF was initiated either by photoirradiation of bis-(2,4,6-trimethylbenzyl) phenylphosphine oxide or by chemical initiation in the presence of ammonium persulfate and ascorbic acid. The cross-linking of OPF was qualitatively investigated by NMR spectroscopy. FIG. 8 shows the changes in the NMR spectrum of OPF 3.4K after cross-linking. Photoirradiation for 30 min cross-linked the OPF caused the NMR band of unsaturated fumarate protons at 6.8 ppm to disappear and the PEG proton peak to dramatically broaden. The fumarate protons were consumed in the cross-linking reaction. The inventors, while not wishing to be limited by the following interpretation, believe that the peak broadening may be related to decreased polymer mobility and thus a shorter relaxation time.

Figure 9:
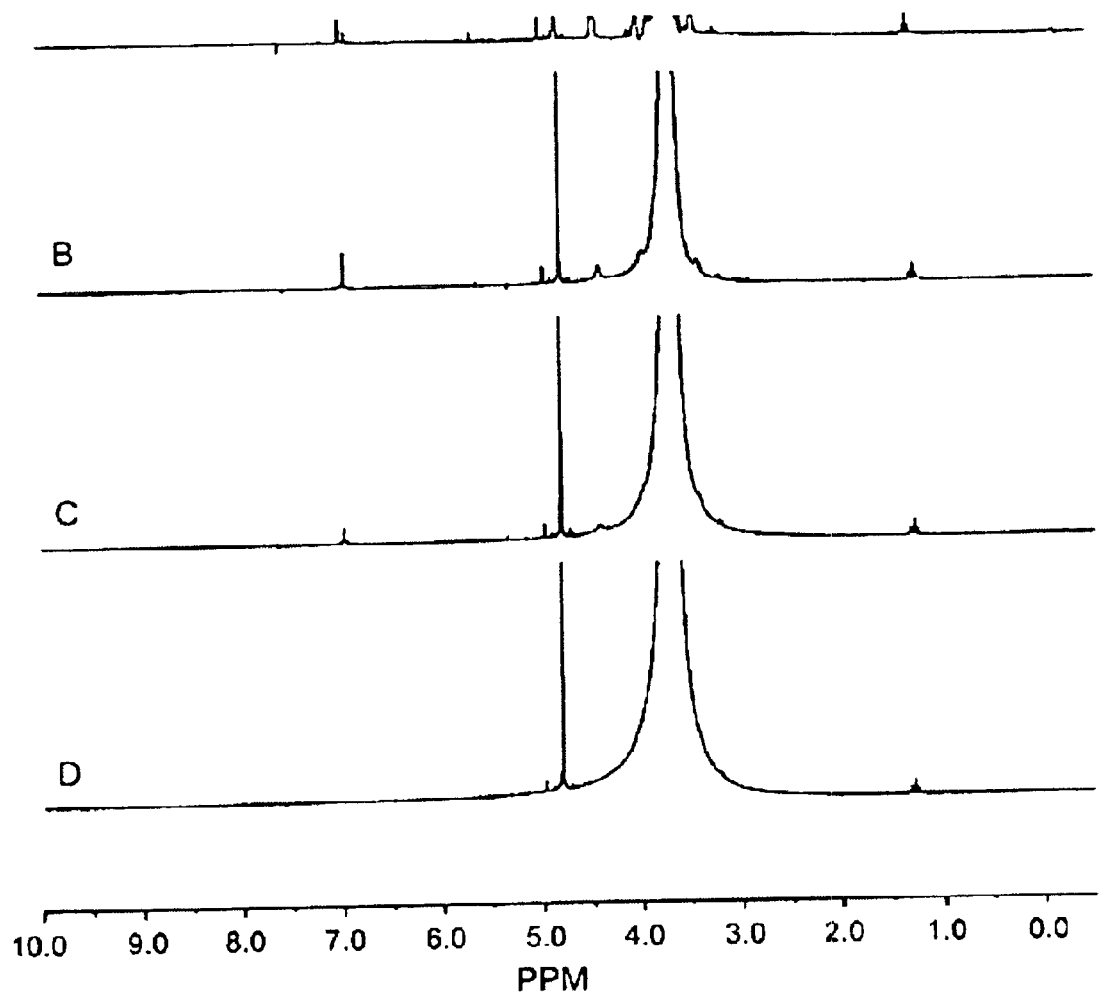
FIG. 9 is a plot showing $^1$H NMR spectra of OPF 3.4K at 10 min (A), 1.5 h (B), 3.0 h (C), and 24 h (D) after the addition of ammonium persulfate and ascorbic acid, where the NMR was measured in D$_2$O and the peak assignment of OPF was based on the chemical structures and notions in FIG. 3.

In addition to photoirradiation of the OPF, radical polymerization using ammonium persulfate and ascorbic acid also cross-linked the OPF 3.4K. The chemical initiators required a longer time for the cross-linking of OPF than that needed with photoirradiation. Ten minutes after the addition of initiators, there was no significant change in the NMR spectrum of the OPF 3.4K (FIG. 9A). After further time, the intensity of the fumarate proton peak noticeably decreased and the PEG proton peak broadened (FIGS. 8B, C, and D). The OPF 3.4K started to form a gel at 3 h. The complete crosslinking of the OPF 3.4K caused the fumarate proton peak, b, to disappear in the NMR spectrum and the PEG proton peaks to broaden further as shown in FIG. 9D.

While not wishing to be limited to the following interpretation, the inventors believe that the presumed random coils of PEG in 60% v/v DMF in water might help the OPF cross-link.

Characterization of Swelling of the Cross-Linked OPF

The cross-linked OPF exhibited swelling characteristics of a hydrogel, with swelling ratios dependent on the molecular weight of PEG. Table 2 summarizes the results of the swelling studies. As the PEG molecular weight increased from 1000 to 4600, the swelling ratio of the cross-linked OPF by photo-irradiation in the presence of 1.0% w/w initiator increased from 5.7 to 16.0. However, the concentration of the initiator did not significantly affect the swelling of the cross-linked OPF in the range from 1.0% w/w to 2.0% w/w. The increase in the swelling ratio with the increase in the PEG molecular weight may be due to the longer mesh size between cross-linkable fumarate bonds. As seen in Table 2, the sol fraction of the cross-linked OPF also increased with the increase in PEG molecular weight. The sol fraction of cross-linked OPF at 1.0% w/w of initiator increased from 8.6 to 19.8% as the PEG molecular weight increased from 1000 to 4600.

TABLE 2

Swelling Properties of the Cross-linked OPF Hydrogels

| Sample | r | Initator (% w/w) | swelling ratio | sol fraction (%) |
|---|---|---|---|---|
| OPF 1.0K | 0.90 | 1.0 | 5.67 ± 0.10 | 8.61 ± 0.24 |
| OPF 1.0K | 0.90 | 1.5 | 6.62 ± 0.04 | 10.48 ± 0.12 |
| OPF 1.0K | 0.90 | 2.0 | 5.91 ± 0.04 | 6.10 ± 0.11 |
| OPF 3.4K | 0.90 | 1.0 | 11.55 ± 0.61 | 11.65 ± 3.80 |
| OPF 3.4K | 0.90 | 1.5 | 12.61 ± 0.07 | 12.18 ± 0.16 |
| OPF 3.4K | 0.90 | 2.0 | 13.22 ± 0.10 | 12.15 ± 0.10 |
| OPF 4.6K | 0.90 | 1.0 | 16.01 ± 0.16 | 19.79 ± 0.10 |
| OPF 4.6K | 0.90 | 1.5 | 18.44 ± 0.21 | 20.06 ± 0.68 |
| OPF 4.6K | 0.90 | 2.0 | 19.91 ± 0.21 | 21.10 ± 0.41 |
| OPF 1.0K | 0.98 | 1.5 | 5.35 ± 0.07 | 5.87 ± 0.06 |
| OPF 1.0K | 0.80 | 1.5 | 11.03 ± 0.40 | 53.51 ± 1.00 |

$^a$r is the molar ratio between fumaryl chloride and PEG. For all samples, n=3.

The molar ratio of fumaryl chloride to PEG also affected the swelling of crosslinked OPF. As r increased from 0.80 to 0.98, the swelling ratio of the cross-linked OPF 1.0K in the presence of 1.5% w/w of photo-initiator decreased from 11.0 to 5.4. The change in swelling ratio of the cross-linked OPF 1.0K with the change in the reactant molar ratio may be associated with the change in sol fraction. The sol fraction of the cross-linked OPF 1.0K slightly increased from 6 to 10% as the reactant molar ratio decreased from 0.98 to 0.90, respectively. Further decrease in r from 0.90 to 0.80, however, dramatically increased the sol fraction from 10 to 54%, respectively, while the swelling ratio increased from 6.6 to 11.0. The effect of the molar ratio on the sol fraction might result from the change in the molecular weight of the OPF 1.0K. As r increased from 0.80 to 0.98, the determined molecular weight by GPC increased from 4990 to 7790. The increase in molecular weight caused an increase in viscosity of the OPF 1.0K solution. This increase in viscosity might affect the crosslinking by limiting the diffusion of radicals. As the viscosity increases, the limited diffusion of radicals may interfere with the termination of polymerization by bimolecular coupling.

Conclusion

Exemplary macromers based on PEG and fumaric acid was successfully prepared by a reaction between PEG and fumaryl chloride. The exemplary macromers were designed to contain end PEG chains and multiple fumarate bonds. The PEG molecular weight and the molar ratio of PEG and fumaryl chloride affected the molecular weight of OPF and its physical properties. The prepared OPF was cross-linked by radical polymerization initiated by photoirradiation and chemical initiation. The cross-linked OPF gels exhibited typical properties of hydrogels, which were dependent on the molecular weight of PEG and the reactant ratio between fumaryl chloride and PEG.

II. Functionalized Oligo(Poly(Ethylene Glycol)Fumarate Macromers

Materials

Poly(ethylene glycol) of molecular weight 1000 (PEG 1.0K), triethylamine, trifluoroacetic anhydride, diethyl fumarate, propylene glycol, calcium hydride, and 4-nitrophenyl chloroformate (NPC) were purchased from Aldrich (Milwaukee, Wis.) and were used as received. Fumaryl chloride was obtained from Acros (Pittsburgh, Pa.) and distilled before use. Gly-Arg-Gly-Asp (GRGD) was purchased from Bachem California Inc. (Torrance, Calif.). Bis-(2,4,6-trimethylbenzyl) phenylphosphine oxide was supplied by Ciba Specialty Chemicals (Terrytown, N.Y.).

Methylene chloride was purified by distillation after refluxing 4 hr over calcium hydride. All other solvents were of reagent grade and were used as received.

General Procedures

Activation of OPF and Modification of the Activated OPF with GRGD

Figure 2:
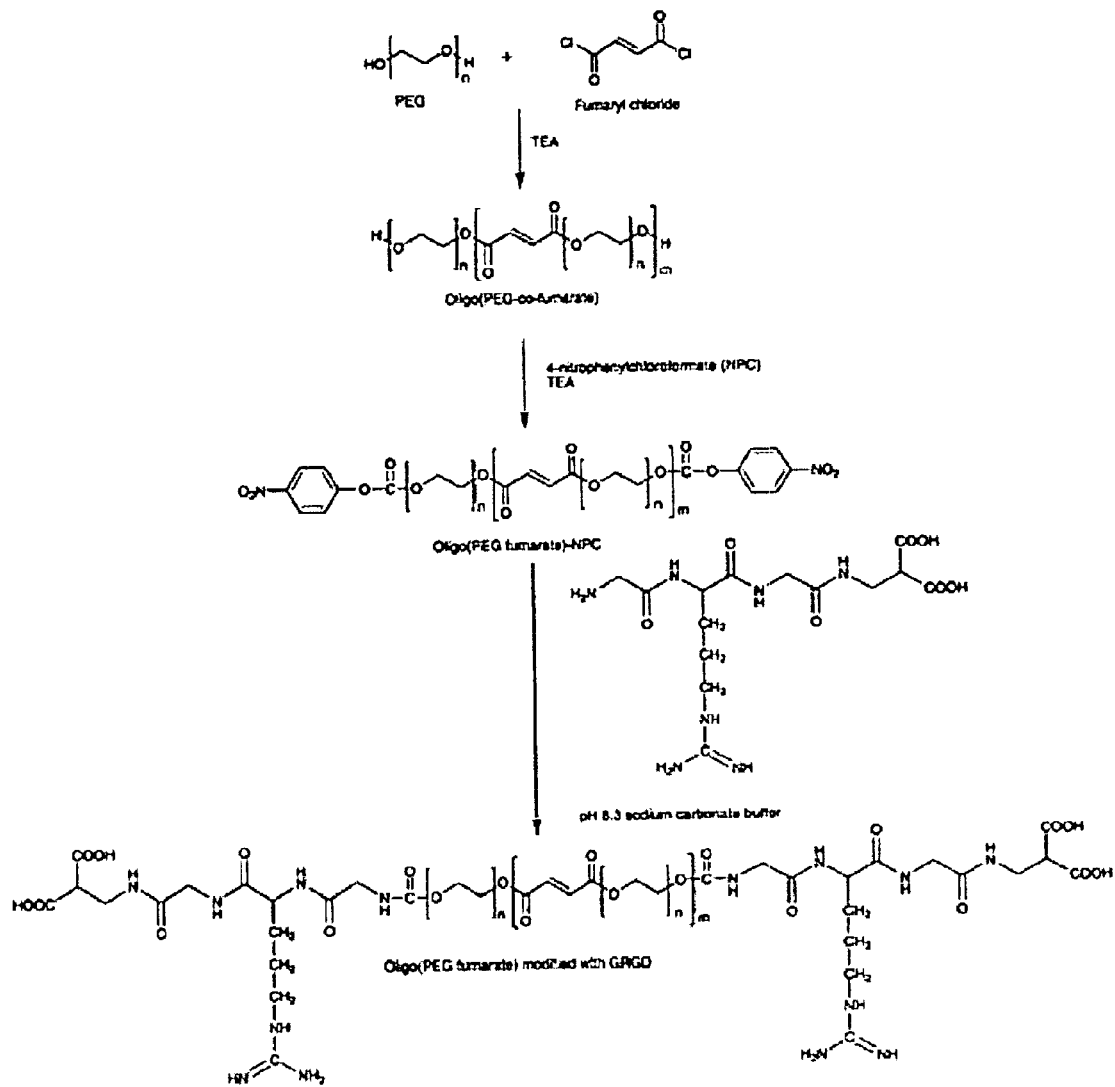
FIG. 2 is a schematic chemical diagram illustrating the preparation of the OPF 1.0K and its GRGD modification.

A new PEG macromer, oligo(PEG fumarate) (OPF), was synthesized and modified as shown schematically in FIG. 2. PEG 1.0K was reacted with fumaryl chloride to result in OPF 1.0K described above in Section I. Briefly, after drying 30 g of PEG 1.0K (30 mmoles) by azeotropic distillation using 200 ml of toluene, the dried PEG 1.0K were reacted with 27 mmoles of fumaryl chloride in the presence of 27 mmoles of triethylamine on ice. The resulting OPF 1.0K was purified by recrystallization using 500 ml of ethyl acetate. The number average molecular weight ($M_n$) of OPF 1.0K was determined to be 5340 through end group analysis using NMR spectroscopy. The spectra were obtained after OPF 1.0K was dissolved in 5.0% v/v trifluoroacetic anhydride in $CDCl_3$.

The OPF 1.0K was reacted with 4-nitrophenyl chloroformate (NPC) before modification with GRGD. Ten grams of OPF 1.0K (1.9 mmoles) were dried by azeotropic distillation of 80 ml out of 100 ml toluene. The OPF 1.0K was then dissolved in 100 ml anhydrous methylene chloride and reacted with 4.2 g NPC (21 mmoles) in the presence of 3.7 ml triethylamine (26 mmoles) on ice for 2 hr. After running the reaction for another 16 hr at room temperature, the solvent was removed by rotovaporation. The concentrate was dissolved in 300 ml ethyl acetate and filtered to remove precipitates of triethylamine hydrochloride salt. The OPF 1.0K activated with NPC (NPC-OPF 1.0K) was purified twice by recrystallization in ethyl acetate. Finally, the NPC-OPF 1.0K was dried under reduced pressure and stored at 5° C. to minimize hydrolysis.

The activated NPC-OPF 1.0K (0.055 g, 0.103 mmole) was reacted with GRGD (5 mg, 0.109 mmole) in 5 ml of 0.1M sodium bicarbonate buffer of pH 8.3. The reaction was run overnight at room temperature. In order to remove unreacted GRGD and released 4-nitrophenol, the reaction mixture was dialyzed using deionized distilled water (DDW) for 2 days with periodic medium changes. A regenerated cellulose ester membrane (MWCO=2000, Spectra/Por) was used. The dialyzed polymer solution was immediately frozen in liquid nitrogen and lyophilized for 2 days.

The OPF 1.0K, NPC-OPF 1.0K, and the OPF 1.0K modified with GRGD were characterized by a 250 MHz $^1$H-NMR spectrometer (Bruker AC 250) in $CDCl_3$. FT-IR spectra of KBr pellets of OPF and its derivatives were acquired by using a Nicolet 500 spectrometer (Madison, Wis.).

Preparation of the Cross-Linked PPF Incorporated with the GRGD Modified OPF 1.0K An unsaturated biodegradable polyester, poly(propylene fumarate) (PPF), was prepared by the method described in co-pending application Ser. No. PCT/US99/07912, filed Apr. 9, 1999, and entitled "Synthesis of Poly (Proplyene Fumarate) by Acylation of Propylene Glycol in the Presence of a Proton Scavenger," which is incorporated herein by reference. Briefly, diethyl fumarate was reacted with propylene glycol at 145° C. in the presence of a catalytic amount of zinc chloride to produce bis-(2-hydroxypropyl) fumarate. The molar ratio of diethyl fumarate to propylene glycol was 1:3. Hydroquinone was added to avoid undesired cross-linking of PPF while at elevated temperature. The bis-(2-hydroxypropyl) fumarate was transesterified for 4 hr at 150° C. and 0.1 torr. After the transesterification, the reaction mixture in ethyl acetate was washed with 5.0 w/v % hydrochloric acid to remove zinc chloride. The mixture was concentrated by rotovaporation and PPF was precipitated with ether. The $M_n$ of the PPF, as determined by gel permeation chromatography (GPC), was 1630.

A polymeric network was prepared from PPF and OPF 1.0K modified with GRGD. Varying amounts of PPF and OPF 1.0K modified with GRGD were mixed in the presence of 1 ml of methylene chloride and 20 µl of N,N-dimethylformamide (DMF). The compositions of the polymer solutions used are presented in Table 3. For photo-cross-linking, 0.5% w/w of bis-(2,4,6-trimethylbenzyl) phenylphosphine oxide to PPF was added to the polymer mixture. The polymer mixture was spread on a clean glass plate equipped with 0.2 mm high spacers. After placing a second glass plate on the spacers and covering the polymer film, the polymer mixture was cross-linked by photoirradiation for 30 min in an Ultralum (Paramount, Calif.) ultraviolet light box. The cross-linked PPF film was thoroughly washed with DDW and dried overnight at 50° C. in a vacuum oven.

TABLE 3

Compositions of the polymer mixtures for the preparation of the cross-linked PPF. GRGD-OPF 1.0K stands for the OPF 1.0K modified with GRGD.

| Sample | PPF (g) | OPF 1.0K (mg) | GRGD - OPF 1.0K (mg) |
|--------|---------|---------------|----------------------|
| Sample 1 | 0.45 | 0 | 0 |
| Sample 2 | 0.45 | 2 | 0 |
| Sample 3 | 0.45 | 20 | 0 |
| Sample 4 | 0.45 | 0 | 2 |
| Sample 5 | 0.45 | 0 | 10 |
| Sample 6 | 0.45 | 0 | 20 |

Characterization of the Cross-Linked PPF

The cross-linked PPF was characterized by FT-IR and contact angle analysis. FT-IR spectra of the cross-linked PPF films were acquired by a Nicolet 500 spectrometer after drying the cross-linked PPF overnight at 0.1 torr. The equilibrium contact angle of 6 µl of DDW on the cross-linked PPF was measured using a NRL contact angle goniometer (Rame Hart, Calif.). Measurements were taken at 4 different locations on the surface of each film.

Results

Synthesis and Modification of OPF 1.0K

Figure 10:
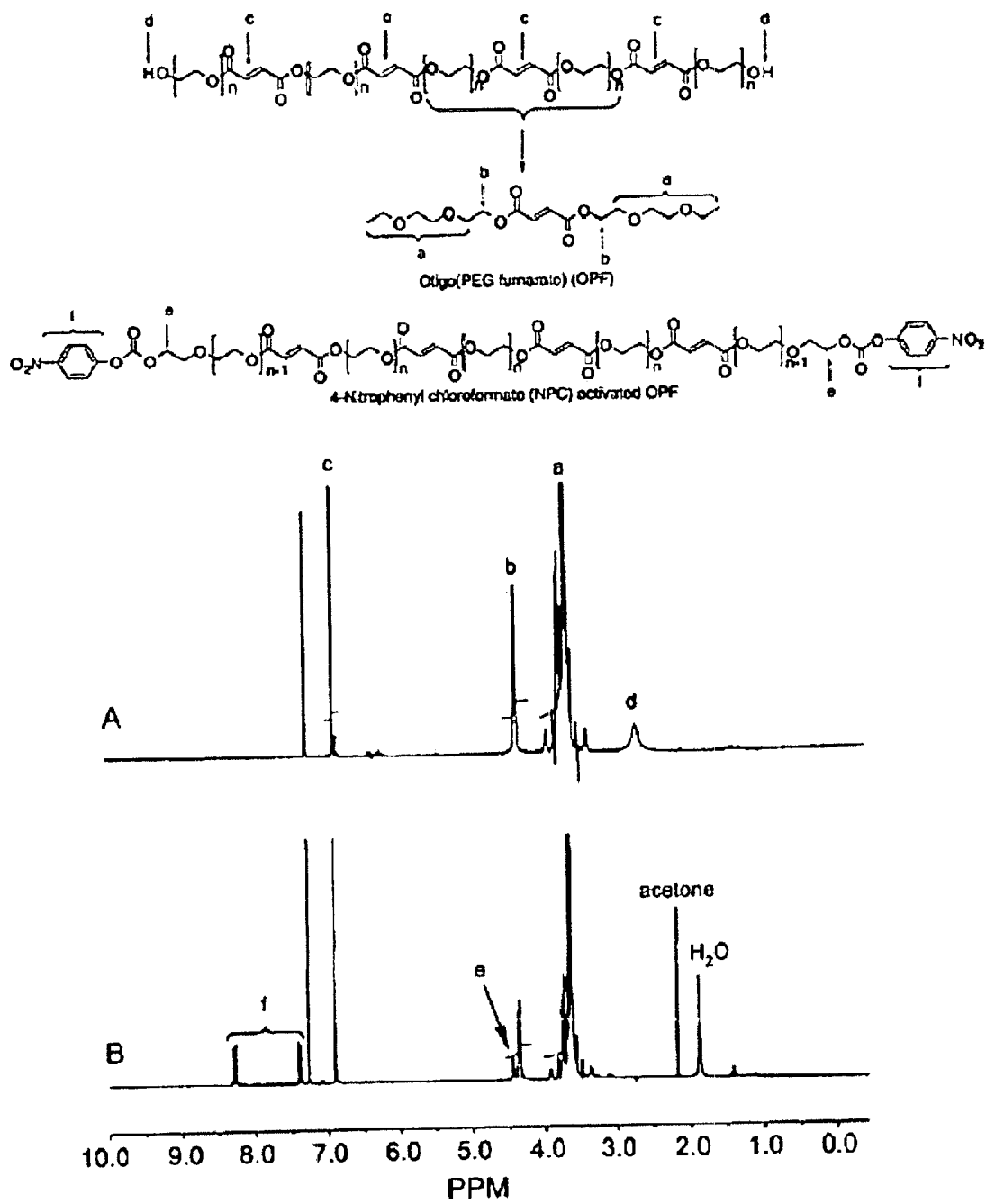
FIG. 10 is a plot showing NMR spectra of the OPF 1.0K (A) and the OPF 1.0K activated with 4-nitrophenyl chloroformate (B) in CDCl$_3$.

The reaction between PEG 1.0K and fumaric acid resulted in the oligomer, OPF 1.0K, as described above in Section I. End group analysis using a NMR measurement showed the number-average molecular weight ($M_n$) of OPF 1.0K was 5340. This analysis also demonstrated that OPF 1.0K had PEG end blocks that were available for future coupling with bioactive molecules such as proteins and peptides. The end hydroxyl groups of PEG reacted with NPC creating an activated OPF. The activated OPF could then be modified with GRGD, a model cell-modulating peptide. The NPC-OPF 1.0K was characterized by NMR (FIG. 10). The characteristic proton peaks of 4-nitrophenyl carbonate ranging from 7.4 to 8.4 ppm in the NMR spectrum (FIG. 10B) indicate the successful activation of OPF by NPC. The NMR spectrum in FIG. 10B also shows that the hydroxyl proton peak of the OPF 1.0K, peak d, disappeared and the proton peak of the methylene group attached to 4-nitrophenyl carbonate, peak e, appeared at 4.4 ppm after activation. NMR analysis also gives a reaction yield of 91% for OPF 1.0K with NPC. This NPC-OPF 1.0K is available for coupling of proteins and peptides in a buffered solution of pH between 8.0 and 9.0.

Figure 11:
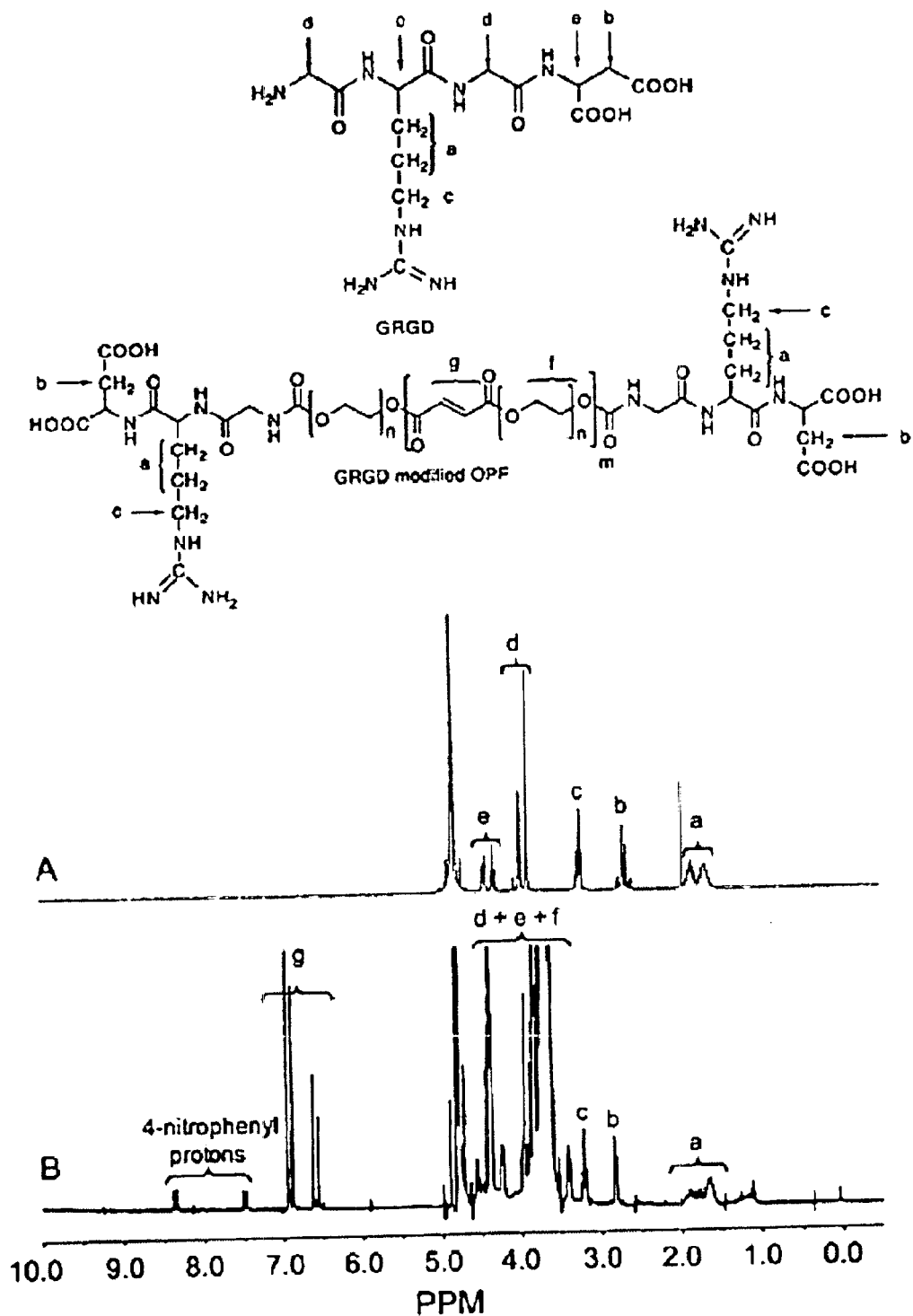
FIG. 11 is a plot showing NMR spectra of GRGD (A) and the OPF 1.0K modified with GRGD (B) in D$_2$O.

The NMR spectrum of OPF 1.0K modified with GRGD in FIG. 11B shows the characteristic proton peaks of GRGD as well as proton peaks of the OPF 1.0K indicating successful modification. The presence of GRGD was confirmed by peaks a, b and c of arginine and aspartic acid. Turning the color of the reaction medium into green during the reaction directly supported the release of 4-nitrophenol by aminolysis. Peak integration of the NMR spectrum gives an 83% yield for the coupling reaction of GRGD with OPF 1.0K.

Figure 12:
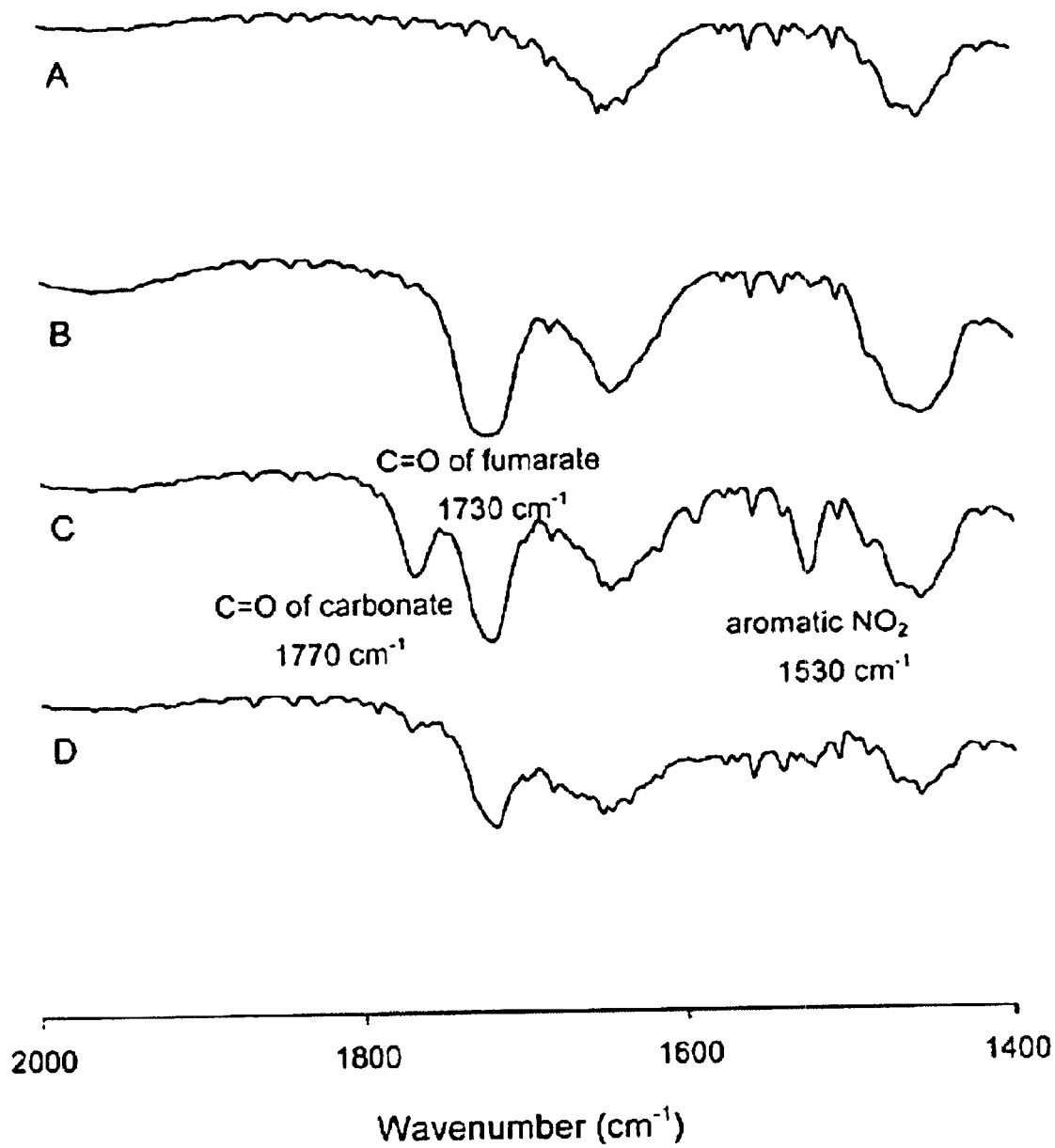
FIG. 12 is a plot showing FT-IR spectra of PEG (A), OPF 1.0K (B), the OPF 1.0K activated with NPC (C), and the OPF 1.0K modified with GRGD (D)

The modified OPF 1.0K was also characterized by FT-IR. As shown in FIG. 12, the IR spectrum of the OPF 1.0K has the —C=O stretch band of fumarate bonds at 1730 cm$^{-1}$ before activation with NPC. The FT-IR spectrum of the NPC-OPF 1.0K has the —C=O stretch band from 4-nitrophenyl carbonate at 1770 cm$^{-1}$, the aromatic —NO$_2$ band at 1530 cm$^{-1}$, as well as the —C=O stretch band of the fumarate bonds. The bands of NPC disappeared after the GRGD modification. The coupling of GRGD with NPC-OPF 1.0K release 4-nitrophenol as supported by the absence of the 4-nitrophenyl bands in the IR spectrum of OPF modified with GRGD.

Figure 13:
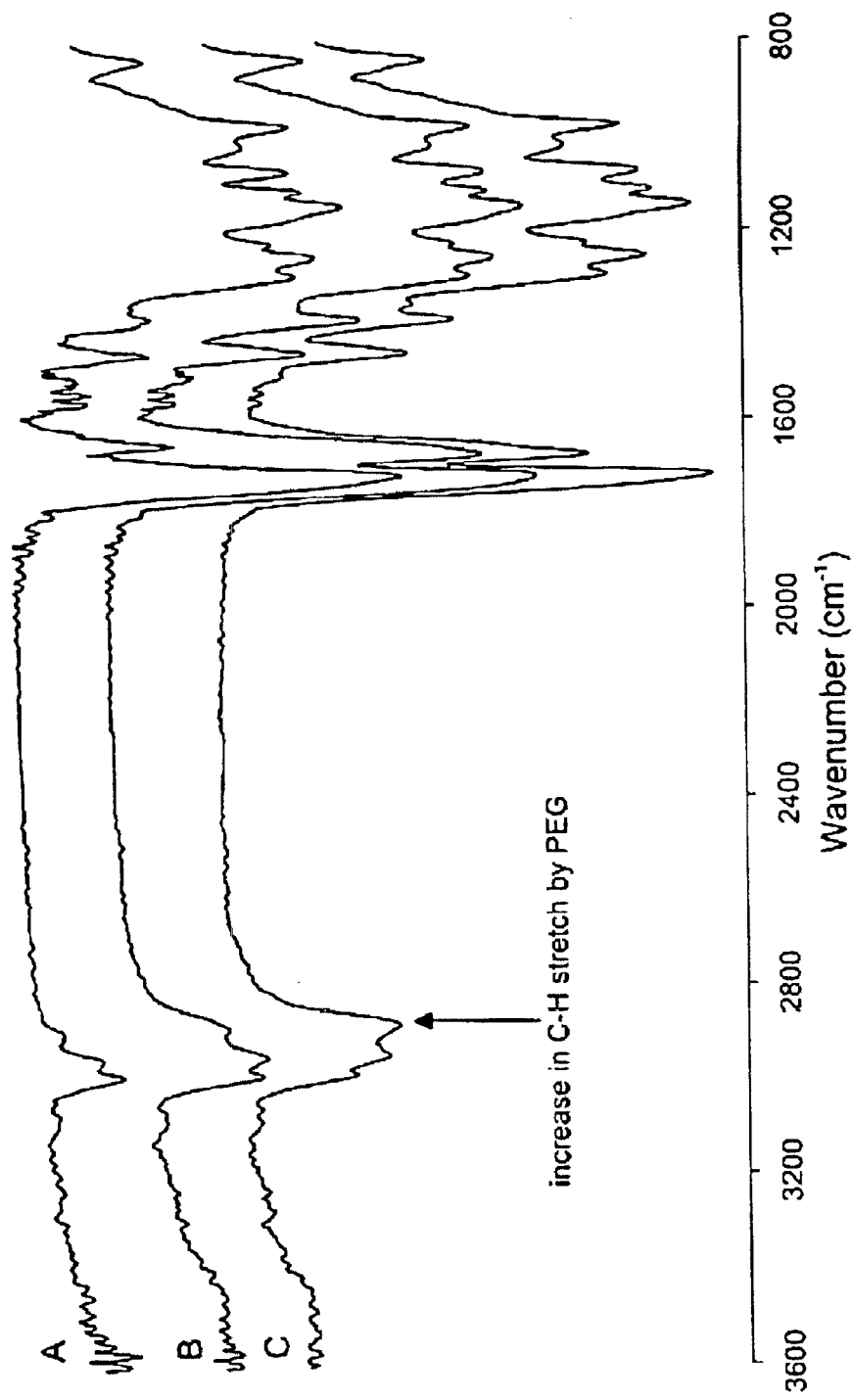
FIG. 13 is a plot showing FT-IR spectra of the cross-linked PPF in the absence (A) and presence of 0.44 w/w % (B) and 4.4 w/w % OPF 1.0K (C)

Preparation and Characterization of a Biodegradable Polymeric Scaffold of PPF and OPF 1.0K Modified with GRGD GRGD modified OPF 1.0K was cross-linked with PPF to prepare a functionalized polymeric network that incorporated cell adhesion peptides. Since the OPF 1.0K and PPF carry unsaturated double bonds, the cross-linking between them is likely through radical polymerization between these bonds. Photo-cross-linking using bis-(2,4,6-trimethylbenzyl) phenylphosphine oxide is highly effective for the cross-linking of a fumarate based macromer as described above in Section I. The cross-linked polymeric network was characterized by FT-IR after drying. The IR spectrum of cross-linked PPF in the absence of OPF 1.0K has three C—H stretch bands at 2890, 2950, and 2990 cm$^{-1}$ (FIG. 13). The incorporation of OPF 1.0K increases the intensities of the bands at 2890 and 2950 cm$^{-1}$. The increase in the C—H stretch band intensity resulted from the additional effect of the C—H band at 2895 cm$^{-1}$ of the PEG incorporated in the OPF. When the concentration of OPF 1.0K increases to 4.4% w/w, the spectral change in the C—H stretch region is more noticeable (FIG. 13-C).

Figure 14:
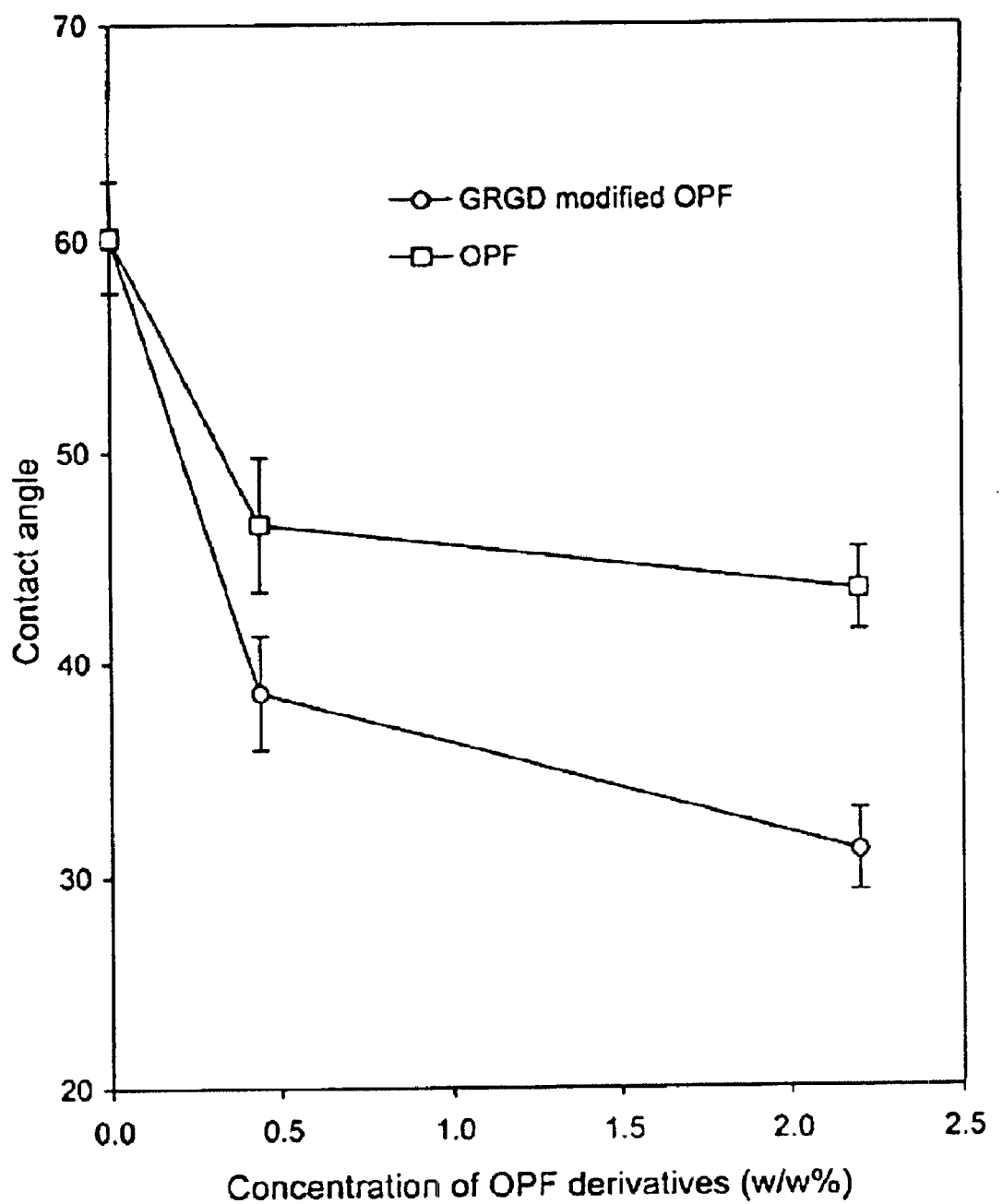
FIG. 14 is a plot showing changes in the equilibrium contact angle of water on the cross-linked PPF with the concentration changes in the OPF 1.0K (■) and the OPF 1.0K modified with GRGD (♦), where N=3 for standard deviation.

Characterization of the film surfaces was conducted to ascertain the changes in surface physical properties with the incorporation of the OPF 1.0K or GRGD modified OPF 1.0K. OPF 1.0K/PPF films (0.44 w/w %) show a decrease in equilibrium water contact angle (46.6°) as compared to PPF films (60.1°) due to the hydrophilic nature of OPF (FIG. 14). A further decrease (43.4°) was seen with an increase in OPF 1.0K concentration (2.2% w/w). The decrease in contact angle change suggests the presence of the OPF 1.0K at the surface of the films. Incorporation of GRGD modified OPF1.0K into films with PPF had a greater effect on the decrease of the equilibrium contact angle of the films than incorporation of OPF 1.0K. Films with a concentration of 0.44% w/w have a contact angle of 38.6°, while 2.2% w/w films have a contact angle of 31.1°. The contact angle measurements indicate that OPF 1.0K modified with GRGD is more hydrophilic than OPF 1.0K alone.

Conclusions

A novel macromer, OPF, was successfully prepared from biocompatible components, PEG and fumaric acid. The prepared OPF was reacted with NPC for its modification with bioactive molecules such as GRGD for possible applications in tissue engineering. The NPC-OPF could be modified with GRGD by aminolysis in a basic buffer solution. The OPF modified with GRGD was cross-linked with PPF to construct a biodegradable polymeric scaffold. The fumarate bonds of OPF and PPF might be involved in the cross-linking by radical polymerization. FT-IR and contact angle measurements were used for characterization of the cross-linked PPF incorporating the OPF modified with GRGD. The water contact angle on the cross-linked PPF decreased as the concentration of OPF or the OPF modified with GRGD increased. Especially, the OPF modified with GRGD exhibited decreased contact angle more than OPF without modification. The OPF modified with bioactive peptides holds promise for the preparation of functionalized polymeric networks.

While preferred embodiments of this invention have been shown and described, modifications thereof can be made by one skilled in the art without departing from the spirit or teaching of this invention. The embodiments described herein are exemplary only and are not limiting. Many variations and modifications of the macromers and methods of making them are possible and are within the scope of the invention. For example, the steps of a method may be carried out in any order unless indicated otherwise. Accordingly, the scope of protection is not limited to the embodiments described herein, but is only limited by the claims that follow, the scope of which shall include all equivalents of the subject matter of the claims.

The Sequence Listing appended hereto is hereby incorporated herein by reference.

What is claimed is:

1. A polymeric network comprising oligo(poly(ethylene glycol) fumarate) wherein the network comprises oligo(poly(ethylene glycol)) cross-linked with oligo(poly(ethylene glycol)fumarate).

2. The polymeric network according to claim 1 modified with a therapeutic agent.

3. The polymeric network according to claim 2 wherein said therapeutic agent comprises a biocompatible organic group selected from the group consisting of peptides, proteins, proteoglycans, glycoproteins, and carbohydrates.

4. The polymeric network according to claim 3 wherein said therapeutic agent comprises a peptide selected from the group consisting of RGD, YIGSR, REDV, IKVAV, and KRSR peptides.

5. The polymeric network according to claim 3 wherein the protein is selected from the group consisting of members of the transforming growth factor beta superfamily, bone morphogeneic proteins, basic fibroblast growth factor, platelet derived growth factor, insulin like growth factor, osteopontin, osteonectin, osteocalcin, bone sialoprotein and other extracellular matrix molecules.

6. The polymeric network according to claim 3 wherein the peptides comprise fragments of the proteins selected from the group consisting of members of the transforming growth factor beta superfamily, bone morphogeneic proteins, basic fibroblast growth factor, platelet derived growth factor, insulin like growth factor, osteopontin, osteonectin, osteocalcin, bone sialoprotein, and other extracellular matrix molecules comprising 3–30 amino acids.

7. The polymeric network according to claim 3 wherein the carbohydrate is selected from the group consisting of starch, cellulose, and chitin.

8. The polymeric network according to claim 1 wherein said polymeric network is water-swellable.

9. A method of making an oligo(poly(ethylene glycol) fumarate) (OPF) coupled to a therapeutic agent, comprising:

(a) providing an OPF;

(b) activating the OPF by dissolving dried OPF and a corresponding amount of 4-nitrophenylchloroformate in triethyl amine; and (c) coupling the therapeutic agent to the activated OPF.

10. The method according to claim 9 wherein the therapeutic agent comprises a biocompatible organic group is selected from the group consisting of peptides, proteins, proteoglycans, glycoproteins, and carbohydrates.

11. The method according to claim 9 further comprising:

(d) cross-linking the OPF with an unsaturated linker molecule.

12. A method of making an oligo(poly(ethylene glycol) fumarate) (OPF) coupled to a therapeutic agent, comprising:

(a) providing an OPF;

(b) activating the OPF by reacting a molar excess of fumaryl chloride over PEG; and (c) coupling the therapeutic agent to the activated OPF.

13. A method of making an oligo(poly(ethylene glycol) fumarate) (OPF) coupled to a therapeutic agent, comprising:

(a) providing an OPF;

(b) activating the OPF by succinylation of end hydroxyl groups of OPF with succinic anhydride; and (c) coupling the therapeutic agent to the activated OPF.

* * * * *